United States Patent
Jeon et al.

(10) Patent No.: US 11,779,021 B2
(45) Date of Patent: Oct. 10, 2023

(54) **STRAIN *SERRATIA PLYMUTHICA* GYUN-8 AND USE THEREOF**

(71) Applicant: ANDONG NATIONAL UNIVERSITY INDUSTRY-ACADEMIC COOPERATION FOUNDATION, Gyeongsangbuk-do (KR)

(72) Inventors: Yong Ho Jeon, Gyeongsangbuk-do (KR); Hyeok Tae Kwon, Gyeongsangbuk-do (KR); Youn Mi Lee, Gyeongsangbuk-do (KR)

(73) Assignee: Andong National University Industry-Academic Cooperation Foundation, Gyeongsangbuk-do (KR)

( * ) Notice: Subject to any disclaimer, the term of this patent is extended or adjusted under 35 U.S.C. 154(b) by 176 days.

(21) Appl. No.: 17/506,495

(22) Filed: Oct. 20, 2021

(65) Prior Publication Data

US 2022/0117234 A1    Apr. 21, 2022

(51) Int. Cl.
*A01N 63/20* (2020.01)
*A01P 3/00* (2006.01)
*A01P 21/00* (2006.01)
*C12N 1/20* (2006.01)

(52) U.S. Cl.
CPC ..................... *A01N 63/20* (2020.01)

(58) Field of Classification Search
None
See application file for complete search history.

(56) References Cited

FOREIGN PATENT DOCUMENTS

KR    101066283    9/2011

OTHER PUBLICATIONS

Office Action, App. No. 10-2020-0137031, dated Oct. 21, 2020, 4 Pages.
Yoon, "Biological Control of Red-Pepper Anthracnose using Antagonistic Bacterial," Dated Feb. 2017, 113 Pages.
Written Decision on Registration, App. No. KR10-2020-0137031, dated Aug. 10, 2022, 4 Pages.
Kurze, et al., "Bilogical Control of Fungal Strawberry Diseases," Publication No. D-2001-0305-02R, Plant Disease, May 2001, 6 Pages.
Kim, et al, "Growth Inhibition of Sclerotium Cepivorum Causing Allium White Rot by Serratia plymuthica Producing Chitinase," Korean Journal of Life Science, vol. 13, No. 1, Feb. 2003, pp. 90-98.

*Primary Examiner* — Alton N Pryor
(74) *Attorney, Agent, or Firm* — Berkeley Law & Technology Group, LLP

(57) ABSTRACT

Disclosed are a novel strain *Serratia plymuthica* GYUN-8 and use thereof and, specifically, a *Serratia plymuthica* GYUN-8 strain, a control agent for controlling a plant disease and a plant growth promoter each containing the strain or a culture thereof as an active ingredient, and a method for controlling a plant disease and a method for promoting plant growth each including soaking or drenching a plant or a plant seed in the strain or a culture thereof, wherein the control agent for controlling a plant disease and the plant growth promoter each containing the novel strain *Serratia plymuthica* GYUN-8 have an excellent antagonistic action on plant pathogens and a superior activity to promote seed germination and plant growth, and furthermore, the control agent for controlling a plant disease and the plant growth promoter of the present disclosure, which are microbial preparations using microbes, can solve environmental pollution problems due to the use of conventional chemical pesticides and human toxicity problems due to residual pesticides, and thus are safer and more eco-friendly and can increase the production of plants, leading to very useful effects from an economic view.

8 Claims, 3 Drawing Sheets

Specification includes a Sequence Listing.

| Control group (Group treated with sterile water) | Group treated with culture of *Serratia plymuthica* GYUN-8 strain of present disclosure |

SEQUENCE LISTING

```
<160> NUMBER OF SEQ ID NOS: 1

<210> SEQ ID NO 1
<211> LENGTH: 1052
<212> TYPE: DNA
<213> ORGANISM: Artificial Sequence
<220> FEATURE:
<223> OTHER INFORMATION: Serratia plymuthica GYUN-8 16S rDNA

<400> SEQUENCE: 1
caggcctaac acatgcaagt cgagcggtag cacaggagag cttgctctct gggtgacgag      60
cggcggacgg gtgagtaatg tctgggaaac tgcctgatgt aggggataa ctactggaaa     120 cggtagctaa taccgcataa cgtctacgga ccaaagtggg ggaccttcgg gcctcacgcc    180
atcagatgtg cccagatggg attagctagt aggtggggta atggctcacc taggcgacga    240
tccctagctg gtctgagagg atgaccagcc acactggaac tgagacacgg tccagactcc    300
tacgggaggc agcagtgggg aatattgcac aatgggcgca agcctgatgc agccatgccg    360
cgtgtgtgaa gaaggcctta gggttgtaaa gcactttcag cgaggaggaa gggttcagtg    420
ttaatagcac tgtacattga cgttactcgc agaagaagca ccggctaact ccgtgccagc    480
agccgcggta atacggaggg tgcaagcgtt aatcggaatt actgggcgta aagcgcacgc    540
aggcggtttg ttaagtcaga tgtgaaatcc ccgcgcttaa cgtgggaact gcatttgaaa    600
ctggcaagct agagtcttgt agaggggggt agaattccag gtgtagcggt gaaatgcgta    660
gagatctgga ggaataccgg tggcgaaggc ggccccctgg acaaagactg acgctcaggt    720
gcgaaagcgt ggggagcaaa caggattaga taccctggta gtccacgctg taaacgatgt    780
cgatttggag gttgtgccct tgaggcgtgg cttccggagc taacgcgtta aatcgaccgc    840
ctggggagta cggccgcaag gttaaaactc aaatgaattg acggggcccc gcacaagcgg    900
tggagcatgt ggtttaattc gatgcaacgc gaagaacctt acctactctt gacatccaga    960
```

```
gaactttcca gagatggatt ggtgccttcg ggaactctga gacaggtgct gcatggctgt    1020
cgtcagctcg tgttgtgaaa tgttgggtta ag                                  1052
```

|---|---|
|  |  |

STRAIN *SERRATIA PLYMUTHICA* GYUN-8 AND USE THEREOF

This application incorporates by reference in its entirety the sequence listing provided in the text file submitted using EFS with the original application papers titled "MPNC94468_Sequence listing.txt," having approximately two kilobytes and created on Oct 6, 2021.

BACKGROUND OF THE INVENTION

1. Field of the Invention

The present disclosure relates to a novel strain *Serratia plymuthica* GYUN-8 and to a plant disease control agent and a plant growth promoter each using the strain.

2. Description of the Prior Art

Although the countries over the world have manufactured and used pesticides based on organic compounds until now in order to control plant diseases, problems are occurring such as environmental pollution, human toxicity due to residual pesticides, and the emergence of pathogens resistant to pesticides. Therefore, eco-friendly plant disease control (biological control) technology through microbes, such as bacteria or fungi, is drawing attention as a plant disease control technology that is employed instead of synthetic organic pesticides.

Chili pepper, which is a tropical plant, is established as a major economic crop in Korea, and occupies the largest cultivation area among seasoning vegetables. However, chili pepper is also a crop that suffers from various diseases due to repeated cultivation, small-scale cultivation, labor integration, and a long period of cultivation. There are 35 types of chili pepper diseases that have been reported in Korea, of which about types of diseases, such as phytophthora blight, anthracnose, and mosaic disease, have been reported to cause a great damage to the cultivation of chili peppers every year, and chili pepper anthracnose and phytophthora blight cause the most serious damage.

Especially, *C. acutatum* and *C. gloeosporioides* are known as bacteria that directly affect quantity and quality of chili peppers among chili pepper anthracnose bacteria, and in recent years, *C. acutatum* has been reported to mainly cause pepper anthracnose. Chili pepper anthracnose occurs mainly in immature fruits and even after harvest, shows a circular spot that is indented in the form of a water-soaked spot and a yellow, pink, or orange spore mass symptom on the upper part of a lesion site, and has been reported to have strong pathogenicity in chili pepper fruits throughout the entire growth period of a plant.

For the control of this anthracnose, dithianon, carbendazium, chlorothalonill, azoxystrobin, mancozeb, and the like are currently used as chemical pesticide, but these have problems of causing ecosystem destruction and exerting insufficient control effects due to chemical resistance of *C. acutatum*.

Accordingly, biological control agents having weak toxicity and no harm to the environment need to be developed.

PRIOR ART DOCUMENT

Patent Document

Korean Patent No. 10-1066283

SUMMARY OF THE INVENTION

The present inventors have identified *Serratia plymuthica* GYUN-8, which is a novel strain having both an excellent control effect against plant pathogens and a plant growth promoting activity, and verified the usability of the novel strain as a microbial preparation, and therefore, completed the present disclosure.

Accordingly, an aspect of the present disclosure is to provide a *Serratia plymuthica* GYUN-8 strain (accession number: KACC 81140BP), which is an antagonistic bacterium isolated from soil.

Another aspect of the present disclosure is to provide a control agent for controlling a plant disease, the control agent containing a *Serratia plymuthica* GYUN-8 strain or a culture thereof as an active ingredient.

Still another aspect of the present disclosure is to provide a control agent for controlling a plant disease, the control agent containing the *Serratia plymuthica* GYUN-8 strain of the present disclosure or a culture thereof as an active ingredient.

Still another aspect of the present disclosure is to provide a method for controlling a plant disease, the method including soaking or drenching a plant or a plant seed in the *Serratia plymuthica* GYUN-8 strain of the present disclosure or a culture thereof.

Still another aspect of the present disclosure is to provide a plant growth promoter containing the *Serratia plymuthica* GYUN-8 strain of the present disclosure or a culture thereof as an active ingredient.

Still another aspect of the present disclosure is to provide a method for promoting plant growth, the method including soaking or drenching a plant or a plant seed in the *Serratia plymuthica* GYUN-8 strain of the present disclosure or a culture thereof.

In accordance with an aspect of the present disclosure, there is provided a *Serratia plymuthica* GYUN-8 strain (accession number: KACC 81140BP), which is an antagonistic bacterium.

In accordance with another aspect of the present disclosure, there is provided a control agent for controlling a plant disease, the control agent containing the *Serratia plymuthica* GYUN-8 strain of the present disclosure or a culture thereof as an active ingredient.

In an embodiment of the present disclosure, the plant disease may occur in chili pepper.

In an embodiment of the present disclosure, the plant disease may be an anthracnose in chili pepper.

In an embodiment of the present disclosure, the anthracnose in chili pepper may be caused by an infection with *Colletotrichum acutatum*.

In accordance with still another aspect of the present disclosure, there is provided a method for controlling a plant disease, the method including soaking or drenching a plant or a plant seed in the strain of the present disclosure or a culture thereof.

In accordance with still another aspect of the present disclosure, there is provided a plant growth promoter containing the *Serratia plymuthica* GYUN-8 strain of the present disclosure or a culture thereof as an active ingredient.

In an embodiment of the present disclosure, the *Serratia plymuthica* GYUN-8 strain or a culture thereof may have an ability to promote seed germination of a plant or promote growth of a plant.

In an embodiment of the present disclosure, the plant may be chili pepper.

In accordance with still another aspect of the present disclosure, there is provided a method for promoting plant growth, the method including soaking or drenching a plant or a plant seed in the strain of claim 1 or a culture thereof.

According to the present disclosure, the control agent for controlling a plant disease and the plant growth promoter each containing the novel strain *Serratia plymuthica* GYUN-8 according to the present disclosure have an excellent antagonistic action on plant pathogens and a superior activity to promote seed germination and plant growth. Furthermore, the control agent for controlling a plant disease and the plant growth promoter of the present disclosure, which are microbial preparations using microbes, can solve environmental pollution problems due to the use of conventional chemical pesticides and human toxicity problems due to residual pesticides, and thus are safer and more eco-friendly and can increase the production of plants, leading to very useful effects from an economic view.

DETAILED DESCRIPTION OF THE EXEMPLARY EMBODIMENTS

Figure 1:
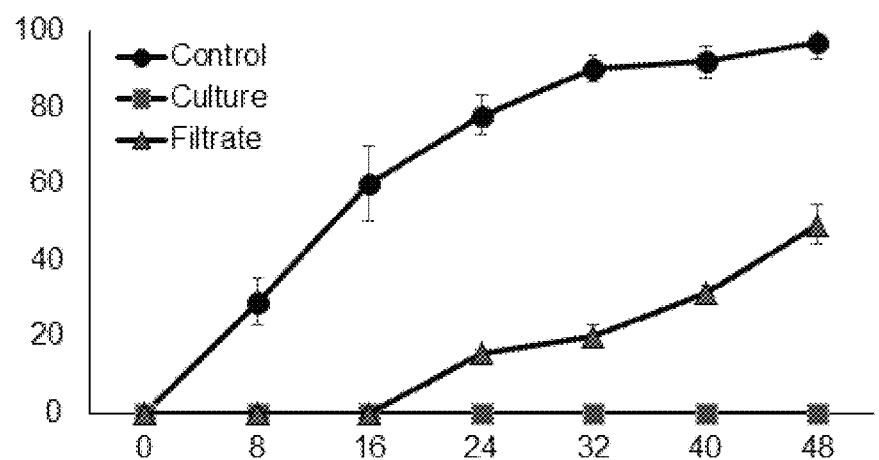
FIG. 1 shows the results of investigating the effects of inhibiting spore germination of the chili pepper anthracnose bacterium *Colletotrichum acutatum* KACC40423 by using a culture and a culture filtrate of the novel strain *Serratia plymuthica* GYUN-8 of the present disclosure.

The present disclosure is characterized by providing a novel strain *Serratia plymuthica* GYUN-8 having both an excellent control effect against plant pathogens and a plant growth promoting activity.

The present inventors, while researching microbes to develop agricultural microbial preparations, identified, from the soil, a novel, previously unknown strain having both an anti-bacterial activity against pathogens and a plant growth promoting activity, named the novel strain "*Serratia plymuthica* GYUN-8", and deposited the novel strain at the Institute of Agricultural Biotechnology on 15 Oct. 2020 to receive the accession number KACC 81140BP.

The novel strain *Serratia plymuthica* GYUN-8 of the present disclosure is characterized by having an excellent control activity against plant pathogens.

In an example of the present disclosure, the activity of a culture and a culture filtrate of the *Serratia plymuthica* GYUN-8 strain to inhibit the spore germination of *Colletotrichum acutatum*, which is a causative bacterium of chili pepper anthracnose, was analyzed. As a result, both the culture and the culture filtrate were shown to inhibit the spore germination of *Colletotrichum acutatum*, wherein a spore germination inhibitory activity of approximately 50% was shown in the group treated with the culture filtrate and spore germination was hardly observed in the group treated with the culture.

In addition, chili pepper fruits were allowed to have anthracnose due to inoculation of an anthracnose pathogen and then treated with a culture of the *Serratia plymuthica* GYUN-8 strain. As a result, the corresponding treatment group showed a control activity of 80% compared with the group treated without the culture.

Therefore, it could be seen from these results that the novel strain *Serratia plymuthica* GYUN-8 was excellent in control activity against plant diseases.

Accordingly, the present disclosure can provide a control agent for controlling a plant disease, the control agent containing a *Serratia plymuthica* GYUN-8 strain or a culture thereof as an active ingredient.

The plant disease may be a plant disease caused in chili pepper, and may be preferably an anthracnose in chili pepper.

The anthracnose in chili pepper is a plant disease caused by an infection with bacteria belonging to *Colletotrichum*, and may be specifically an anthracnose chili pepper caused by an infection with *Colletotrichum acutatum*.

In addition, the control agent for controlling a plant disease according to the present disclosure may use a strain itself that is cultured, or a culture or a culture filtrate of the strain.

The culture may be a culture containing a strain or a culture containing metabolites secreted from the strain, wherein the culture filtrate may be obtained by passing the culture through a filter paper.

A method of treatment with the control agent for controlling a plant disease of the present disclosure may be implemented by soaking or drenching a plant or plant seeds in the *Serratia plymuthica* GYUN-8 strain of the present disclosure or a culture thereof. Soaking or drenching may be conducted for a period of time while the plant or the plant seed can sufficiently react with the strain of the present disclosure or a culture thereof.

The *Serratia plymuthica* GYUN-8 strain of the present disclosure is characterized by having a plant growth promoting activity in addition to a plant disease control effect.

In an example of the present disclosure, chili pepper seeds were treated with a suspension of the *Serratia plymuthica* GYUN-8 strain of the present disclosure and then the degree of germination was checked. The results could verify that the length of germs was longer in the group treated with the suspension of the strain of the present disclosure compared with the group treated without the suspension.

In another example, ports for chili pepper seedlings were drenched in a suspension of the strain of the present disclosure. As a result, the growth of chili peppers was increased by 31.0% in the group treated with the suspension compared with the group treated with tap water.

Accordingly, the present disclosure can provide a plant growth promoter containing a *Serratia plymuthica* GYUN-8 strain or a culture thereof as an active ingredient.

The *Serratia plymuthica* GYUN-8 strain of the present disclosure or a culture thereof has ability to promote plant seed germination or promote plant growth.

Alternatively, the plant may be chili pepper.

Furthermore, the present disclosure can provide a method for promoting plant growth by using the *Serratia plymuthica* GYUN-8 strain of the present disclosure, wherein the method may be implemented through a step of soaking or drenching a plant or plant seeds in a *Serratia plymuthica* GYUN-8 strain or a culture thereof.

Hereinafter, the present disclosure will be described in detail through examples. These examples are given for specifically illustrating the present disclosure, and the scope of the present disclosure is not limited thereto.

EXAMPLE 1

Isolation and Identification of Novel Strain *Serratia plymuthica* GYUN-8

In order to identify a novel strain having both a control effect against plant pathogens and a plant growth promoting activity, the rhizosphere soil of *ginseng* was collected, suspended and diluted in sterile water, and plated on brain heart infusion (BHI), and then microbes forming single colonies were isolated.

Thereafter, the nucleic acid of the isolated soil rhizobacterium was sequenced and the analyzed sequence was compared and analyzed with the strains registered in Genbank by using BLAST of the National Center for Biotechnology Information (NCBI). For the sequencing, 16S rDNA gene of the isolated soil rhizobacterium was PCT amplified using 27F primer (5'-AGAGTTTGATCMTGGCTCAG-3') and 1492R primer (5'-GGYTACCTTGTTACG ACTT-3'). PCR conditions were pre-denaturation (60° C., 2 min), denaturation (98° C., 1 min), annealing (60° C., 1 min), extension (72° C., 1 min), total cycle (30 cycles), and final extension (72° C., 4 min). The amplified PCR product was electrophoresed on a 1% agarose gel in 0.5×TBE buffer (0.045 M Tris-borate, 0.001 M EDTA) at 100 V, 25 mA for 30 min, and then monitored under UV. Thereafter, the PCR product was referred to a DNA sequencing company (Solgent, Daejeon, Korea) and analyzed using Seqman (DNASTAR, USA) program.

As a result, the soil rhizobacterium isolated in the present disclosure is a strain having 99% sequence homology to *Serratia plymuthica*, and this strain was verified to be a novel strain that did not exist before, and was named "*Serratia plymuthica* GYUN-8", which was deposited at the Institute of Agricultural Biotechnology on 15 Oct. 2020 and received the accession number KACC 81140BP. The sequence of 16S rDNA of *Serratia plymuthica* GYUN-8 isolated in the present disclosure is described in SEQ ID NO: 1.

EXAMPLE 2

Analysis of Ability of Present Inventive *Serratia plymuthica* GYUN-8 Strain to Inhibit Spore Germination of Plant Pathogen The activity to inhibit spore germination of the chili pepper anthracnose (*Colletotrichum acutatum* KACC40423) was analyzed using a culture or a culture filtrate obtained by culturing the novel strain *Serratia plymuthica* GYUN-8 of the present disclosure identified in Example 1. For the analysis a spore suspension was obtained and prepared at a concentration of $10^5$ conidia/ml by culturing the chili pepper anthracnose (*Colletotrichum acutatum* KACC40423) in PDA media for 5 days. The culture was prepared by culturing the *Serratia plymuthica* GYUN-8 strain of the present disclosure in BHI liquid media for 3 days and the culture filtrate was prepared by filtering the culture through MF-Millipore filter paper (pore size, 0.22 µm). Thereafter, 10 µl of the spore suspension was dispensed on slide glasses, and treated with 10 µl of the culture or the culture filtrate of the *Serratia plymuthica* GYUN-8 of the present disclosure, separately. During culturing for 25° C. with moisture maintained, the presence or absence of germination and the formation of appressorium were examined for 48 hours at intervals of 8 hours.

The germination of spores was defined as a state when the length of germ tubes was ½ or more of the spore size, and a group treated with sterile water was used as a control group.

As a result of analysis, 97% of spores of *C. acutatum* were germinated for up to 48 hours in the control group treated with sterile water, whereas 49.2% of spores were germinated in the group treated with the culture filtrate of the *Serratia plymuthica* GYUN-8 of the present disclosure, and no germination was observed in the group treated with the culture (see FIG. 1).

It could be therefore seen from these results that the novel strain *Serratia plymuthica* GYUN-8 of the present disclosure had an ability to inhibit the spore germination of plant disease pathogens.

EXAMPLE 3

Analysis of Chili Pepper Fruit Anthracnose Control Effect of Present Inventive *Serratia plymuthica* GYUN-8 Strain Chili pepper fruits were wound, inoculated with an anthracnose pathogen, and then sprayed with a culture of the *Serratia plymuthica* GYUN-8 strain of the present disclosure. Thereafter, the degree of inhibition of anthracnose occurrence was examined.

Figure 2:
FIG. 2 shows the results of investigating the effects of inhibiting chili pepper anthracnose according to the treatment with a culture of the novel strain *Serratia plymuthica* GYUN-8 of the present disclosure.
Figure 2:
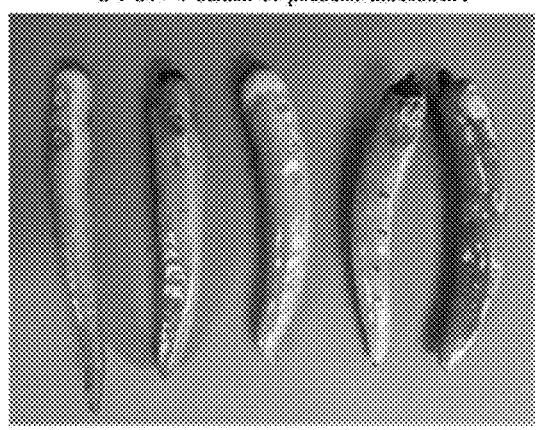

As a result, the occurrence of anthracnose was remarkably inhibited and thus lesions were only partly observed in the group treated with the culture of the *Serratia plymuthica* GYUN-8 strain of the present disclosure compared with the control group (sterile water treatment), and the group treated with the culture of the present disclosure had an anthracnose control activity of 80.02% compared with the control group (see FIG. 2).

EXAMPLE 4

Analysis of Activity of Present Inventive *Serratia Plymuthica* GYUN-8 Strain to Promote Seed Germination and Initial Growth of Chili Pepper Furthermore, in order to investigate whether the *Serratia plymuthica* GYUN-8 strain of the present disclosure had activity to promote plant germination and growth, the strain of the present disclosure was used to analyze the effect of promoting the growth of initial root length of chili pepper.

For the analysis, chili pepper seeds (cv. Korean dark green pepper, Hungnong Seed Company) coatings were completely removed using 1% NaOCl, and the de-coated seeds were cultured on TSA plate media at a temperature of 28° C. for three days, and then the seeds were soaked in a suspension of a $10^7$ CFU/ml suspension of the *Serratia plymuthica* GYUN-8 strain for 30 min. As a control group, a group having seeds soaked in sterile water instead of a suspension was used. The suspension was a suspension obtained by culturing the strain on a solid medium, scraping colonies, and suspending the colonies in sterile water.

Thereafter, the chili pepper seeds were disposed at intervals of 2 cm by using double layered papers (DLP), and subjected to a moist-chamber treatment using zipper packs, followed by culture in an incubator at 25° C. in dark conditions for 6 days. All of the experiments were repeated three times. The length measurement was conducted by measuring the length from the seed portion to the root end.

Figure 3:
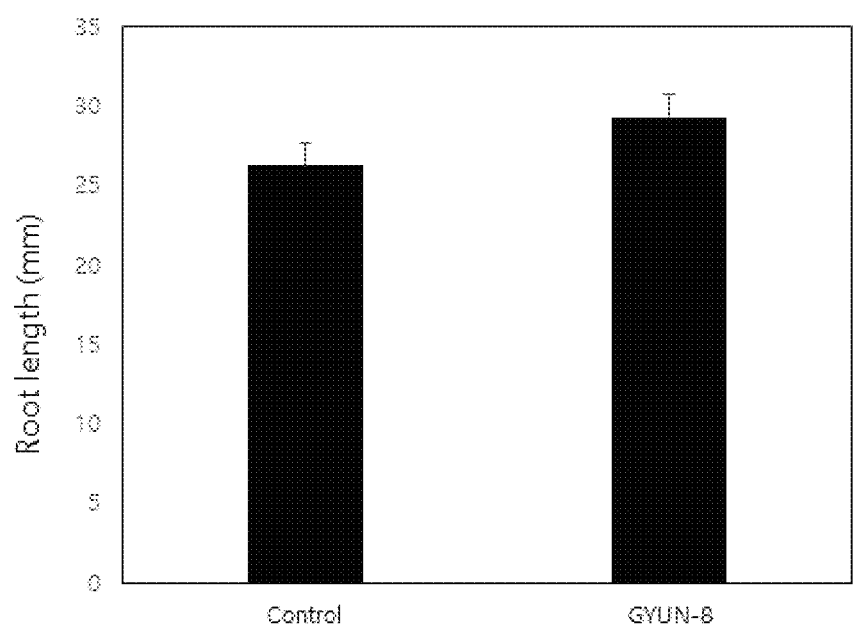
FIG. 3 shows the effects of promoting initial germination of chili pepper seeds according to the presence or absence of the treatment with a suspension of the novel strain *Serratia plymuthica* GYUN-8 of the present disclosure.

As a result, the root length was further increased by 11.43% in the group treated with the suspension of the Serratia plymuthica GYUN-8 strain of the present disclosure compared with the control group (see FIG. 3).

It can be seen from these results that the novel strain Serratia plymuthica GYUN-8 of the present disclosure has an activity to promote plant germination and growth as well as an effect of controlling plant pathogens.

EXAMPLE 5

Analysis of Activity of Present Inventive Serratia Plymuthica GYUN-8 Strain to Promote Chili Pepper Growth In order to investigate whether the Serratia plymuthica GYUN-8 strain of the present disclosure had an activity to promote growth of chili pepper crops, ports for chili pepper seedlings were used to conduct the experiment. The experiment was conducted in a constant-temperature chamber in the clinical plant pathology lab in Andong National University from 20 Sep. to 13 Oct. 2020. For the analysis of promotion of chili pepper growth, the plant length was measured on the ports, and the measurement was repeated three times in all treatment groups in the 36-hole ports. The 36-hole ports (27.5 cm×27.5 cm×3.5 cm) for chili pepper seedlings were filled with bed soil, and then chili pepper seeds (Korean dark green pepper) were seeded one per one hole. The seeds were drenched in the strain of the present disclosure at a concentration of $10 \times 10^7$ CFU/ml with 500 ml for one port from the day of seeding every seven days after the seeds were cultured on TSA plate media. As a control group, a group treated with tap water instead of the strain of the present disclosure was used. The length of growth promotion was measured from the ground part to the top part of chili pepper seedlings.

Figure 4:
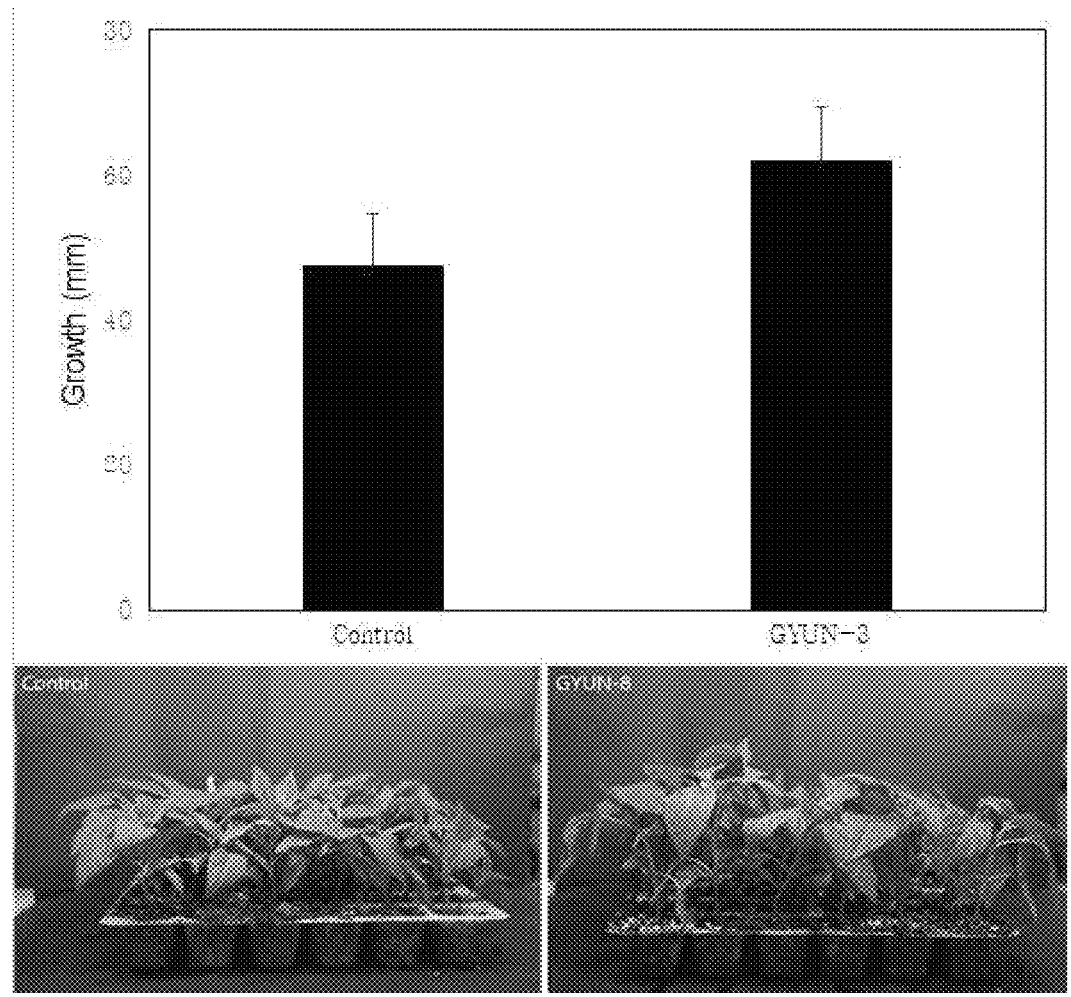
FIG. 4 shows the effects of promoting growth of chili pepper seedlings according to the presence or absence of the treatment with a suspension of the novel strain *Serratia plymuthica* GYUN-8 of the present disclosure.

As a result, as shown in FIG. 4, the growth length of the plant length was further increased by 31.01% in the group treated with the Serratia plymuthica GYUN-8 strain of the present disclosure compared with the control group.

It can be seen through the above experimental results that the Serratia plymuthica GYUN-8 strain of the present disclosure has a plant growth promoting activity as well as an excellent control activity against plant pathogens, and thus can be advantageously used as a control agent for controlling a plant disease and a plant growth promoter for crops.

As set forth above, the present disclosure has been described with reference to preferable examples. A person skilled in the art to which the present disclosure pertain would understand that the present disclosure could be implemented in a modified form without departing from the inherent characteristics of the present disclosure. Accordingly, the examples described herein should be considered from an illustrative aspect rather than from a restrictive aspect. The scope of the present disclosure should be defined not by the detailed description but by the appended claims, and all differences falling within a scope equivalent to the claims should be construed as being included in the present disclosure.

What is claimed is:

1. A *Serratia plymuthica* GYUN-8 strain (accession number: KACC 81140BP), which is an antagonistic bacterium.

2. A control agent effective in controlling a plant disease, the control agent comprising the *Serratia plymuthica* GYUN-8 strain of claim 1 or a culture thereof as an active ingredient.

3. The control agent of claim 2, wherein the plant disease occurs in chili pepper.

4. The control agent of claim 2, wherein the plant disease is an anthracnose in chili pepper.

5. The control agent of claim 4, wherein the anthracnose in chili pepper is caused by an infection with *Colletotrichum acutatum*.

6. A plant growth promoter comprising the *Serratia plymuthica* GYUN-8 strain of claim 1 or a culture thereof as an active ingredient in an effective concentration.

7. The plant growth promoter of claim 6, wherein the *Serratia plymuthica* GYUN-8 strain or a culture thereof has an ability to promote seed germination of a plant or promote growth of a plant.

8. The plant growth promoter of claim 7, wherein the plant is chili pepper.

\* \* \* \* \*